US006548689B1

(12) United States Patent
Pratt, III

(10) Patent No.: US 6,548,689 B1
(45) Date of Patent: Apr. 15, 2003

(54) ALUMINUM COMPOUNDS AND PROCESS OF MAKING THE SAME

(76) Inventor: William E. Pratt, III, 1901 Evans St., Morehead City, NC (US) 28557

( * ) Notice: Subject to any disclaimer, the term of this patent is extended or adjusted under 35 U.S.C. 154(b) by 0 days.

(21) Appl. No.: 09/616,575

(22) Filed: Jul. 14, 2000

Related U.S. Application Data

(60) Provisional application No. 60/144,726, filed on Jul. 20, 1999.

(51) Int. Cl.[7] .................................................. C07F 5/06

(52) U.S. Cl. ....................... 556/183; 556/185; 556/186

(58) Field of Search ................................ 556/183, 185, 556/186

(56) References Cited

U.S. PATENT DOCUMENTS

| | | | | |
|---|---|---|---|---|
| 2,019,415 A | | 10/1935 | Jochem et al. | 260/11 |
| 5,166,408 A | * | 11/1992 | Fried | 554/223 |
| 5,409,501 A | | 4/1995 | Zauns-Huber et al. | 8/94.29 |
| 5,468,892 A | | 11/1995 | de Riese-Meyer et al. | 556/171 |
| 5,772,753 A | * | 6/1998 | Valenti | 106/802 |

FOREIGN PATENT DOCUMENTS

| | | |
|---|---|---|
| DE | 30 01 093 A1 | 7/1980 |
| EP | 0 201 802 A3 | 4/1986 |
| EP | 0 492 827 A1 | 7/1992 |

* cited by examiner

*Primary Examiner*—Porfirio Nazario-Gonzalez
(74) *Attorney, Agent, or Firm*—Nutter McClennen & Fish

(57) ABSTRACT

Novel aluminum compounds with the following empirical formula:

$$AlX_{3-n}(Y)_n$$

wherein=0.01 to 2.99, preferably n=2 to 2.75 are described. Each X, individually, can be an inorganic anion such as halides, alkoxides, hydroxide, nitrate, or perchlorate. Each Y, individually, can be an organic anion such as an organic acid containing from one to six carbon atoms, including but not limited to, acetic acid, hydroxy-acetic acid, oxalic acid, succinic acid, citric acid, maleic acid, adipic acid, glutaric acid, and in particular formic acid. Methods to prepare the novel aluminum compounds are also described. Such aluminum compounds are useful in the preparation of decorative paper.

33 Claims, 1 Drawing Sheet

ALUMINUM COMPOUNDS AND PROCESS OF MAKING THE SAME

CROSS-REFERENCE TO RELATED APPLICATIONS

This application claims priority to U.S. Provisional Patent Application No. 60/144,726, filed Jul. 20, 1999, entitled "Aluminum Compounds and Process of Making the Same", the contents of which are incorporated herein by reference.

BACKGROUND OF THE INVENTION

The papermaking process requires the individual particles of fiber and pigment, e.g., titanium dioxide, be brought together to form the sheet. The process of forming the sheet takes place by dewatering a dilute aqueous dispersion of the papermaking components (i.e., fiber and pigment). However, it is generally recognized that the surface of papermaking components have electrostatic charges. Because of the high surface to volume ratio of the papermaking components, these surface charges play a dominant role in the dewatering process and the formation of the sheet. These surface charges cause subtle interactions between the particles, and as a result, they have a direct impact on both the opacity and the formation of the decor paper. Manipulating these surface charges to enhance the quality of paper is one of the primary purposes of wet end chemistry. Various types of paper can be prepared, dependent upon the amounts of additive(s), fiber(s) and pigment(s).

Decorative laminate is a generalized term used to describe a decorative covering commonly used in the furniture and construction industry. Decorative laminates are composed of resins and paper. The resins provide a protective layer for durability and wear resistance. Decor paper is the surface sheet used to manufacture decorative laminates, it is available in a variety of solid shades and printed patterns.

Historically, decor papers were manufactured by using a combination of alum (aluminum sulfate) and sulfuric acid. Low levels of alum provide for fiber charge neutralization, reducing the fiber-fiber repulsion. The alum is thought to increase the cationicity of titanium dioxide particles present in the papermaking solution. The sulfuric acid is present to control the pH. Sulfuric acid, unlike alum, does not become incorporated in the sheet at reasonable addition levels and therefore does not contribute to sheet pH. The overall effect of using alum and sulfuric acid is improved optical properties and sheet uniformity. This result is obtained because alum provides for a more uniform dispersion of titanium dioxide and it allows the Van der Waals forces to play a more dominant role in the fiber-fiber interaction. However, this approach to manufacturing decor papers is not without limitations and flaws. Minor process variations cause the amount of sulfuric acid and alum needed in the papermaking system to vary widely. Because sulfuric acid is a strong acid, minor changes in the papermaking process lead to great changes in the system pH. Likewise, changing process conditions alter the optimum amount of alum needed for good formation and low sheet pH. Together these factors, (process variations which cause changing but unpredictable sulfuric acid and alum requirements) make it difficult to produce a consistent quality sheet useful for the production of decor sheets.

Recently, aluminum triformate (ATF, $Al(O_2CH)_3$) has been used as a replacement for both alum and sulfuric acid in decor paper manufacturing. Aluminum triformate is less acidic than alum and it does not effect the sheet pH as much as alum does. (The reduced acidity is due to the fact that formate ion coordinates with the aluminum more strongly than the sulfate ion does.) As a result of the reduced acidity, ATF can be used with success for both pH control and charge neutralization in decor paper manufacturing. ATF provides more consistent results than alum and sulfuric acid because ATF is considered to be less sensitive to process variations.

Although, aluminum triformate provides a unique benefit in the manufacture of decor paper, its use is not without complications. ATF is difficult to manufacture, and therefore it has limited availability, and it is expensive. ATF is also difficult to use because of its limited solubility and because of its facile thermal decomposition. U.S. Pat. No. 5,468,892 highlights the difficulties in preparing aluminum triformate. These authors confirm that ATF has many uses but limited availability. *The Kirk Othmer Encyclopedia of Chemical Technology* notes that "most commercial aluminum formate is the monobasic aluminum diformate because of the difficulties involved in aluminum triformate preparation". U.S. Pat. No. 5,468,892 confirms this by stating that ATF is only marketed as a solid or as basic aluminum formates with a considerable content of free hydroxyl groups.

Basic aluminum formates do not have the same reactivity as ATF, and are undesirable when manufacturing decor paper. U.S. Pat. No. 5,468,892 describes the preparation of solutions of ATF via reaction of sodium aluminate with formic acid. Although this approach has some utility, the reaction between the sodium aluminate and formic acid is poor and is uneconomical. Additionally, sodium aluminate contains considerable unreacted alkali. This unreacted alkali consumes formic acid in an unproductive reaction to form sodium formate. Preparation of ATF by the reaction of sodium aluminate with formic acid requires as much as a 70% excess of formic acid. The undesired reaction which consumes formic acid to produce sodium formate, substantially increases the cost of manufacturing ATF by this route. These difficulties preclude there being a readily available and economical source of ATF or ATF derivatives.

As a consequence of these disadvantages, a need therefore exists for an alternative to ATF for the manufacture of paper, and particularly, decor paper.

SUMMARY OF THE INVENTION

The present invention circumvents the problems described above by providing aluminum compounds which can be incorporated into a paper making process at a substantially lower pH than that currently available, that helps to uniformly disperse titanium dioxide in the paper product, thereby helping to increase opacity, and improves the durability of the paper. In a particular embodiment, the aluminum compounds of the invention are compounds having the formula $AlX_{3-n}(Y)_n$. Each X, independently, can be a halide, an alkoxide, a hydroxide, a nitrate, a perchlorate or combinations thereof. Each Y, independently, can be an anion of an organic acid having one to six carbon atoms and the value of n is between about 0.01 and 2.99. For example, the an anion of an organic acid can be acetic acid, hydroxy acetic acid, oxalic acid, succinic acid, citric acid, maleic acid or formic acid with n being between about 2 and 2.75. In a preferred embodiment, X is chloride, Y is formate, and n is between 2 and 2.75.

The aluminum compounds of the invention may be used in a variety of paper applications, including use in decorative laminates such as those decorative coverings commonly used in the furniture and construction industry. The aluminum compounds of the invention are also useful as pigments, catalysts, and in size manufacturing, in paper manufacturing, paint manufacturing, as well as, textile and leather processing. It is understood that the term "aluminum compound" encompasses any aluminum species which falls within the formula $AlX_{3-n}(Y)_n$ as described herein.

The invention provides methods for the preparation of compounds having the formula $AlX_{3-n}(Y)_n$ wherein each X, independently, can be a halide, an alkoxide, a hydroxide, a nitrate, a perchlorate or combinations thereof. Each Y, independently, can be ananion of an organic acid having one to six carbon atoms and the value of n is between about 0.01 and 2.99. The method includes combining between 4 moles and 5 moles of an organic acid having one to six carbon atoms acid with 1 mole of aluminum halohydrate. In preferred embodiments, the organic acid is formic acid or acetic acid and the aluminum halohydrate is polyaluminum chloride, preferably, aluminum chlorohydrate. Preferably, the method produces formic or acetic acid aluminum chlorides where n is between 2 and 2.75, preferably between 2.333 and 2.666. In a particularly preferred embodiment, the method produces an aluminum compound where X is a mixture of chloride and hydroxide and the organic acid is formic acid. Preferably the method produces formic acid aluminum compound/hydroxide/chloride mixtures where n is between 2 and, preferably between 2.333 and 2.666. The resulting product can be used in concentrated form or diluted to obtain a stable solution.

In another aspect, the present invention pertains to methods for preparing a compound having the formula $AlX_{3-n}(Y)_n$ wherein each X, independently, is a halide, an alkoxide, a hydroxide, a nitrate, a perchlorate or combinations thereof. Each Y, independently, is ananion of an organic acid having one to six carbon atoms and the value of n is between about 0.01 and 2.99. The methods include combining about 4 moles of an organic acid having one to six carbon atoms acid with 1 mole of polyaluminumhalide. In one embodiment, the organic acid is formic acid and wherein polyaluminum halide is polyaluminumchloride. In a preferred embodiment, the process produces an aluminum compound where X is chloride and Y is formate. The resulting product can be used in concentrated form or diluted to obtain a stable solution.

All percentages by weight identified herein are based on the total weight of the composition unless otherwise indicated.

BRIEF DESCRIPTION OF THE DRAWINGS

Other objects, advantages and features of the present invention will be readily appreciated as the same becomes better understood by reference to the following detailed description when considered in connection with the accompanying drawing, in which like reference numerals designate like parts throughout the figures thereof and wherein.

DETAILED DESCRIPTION OF THE INVENTION

Figure 1:
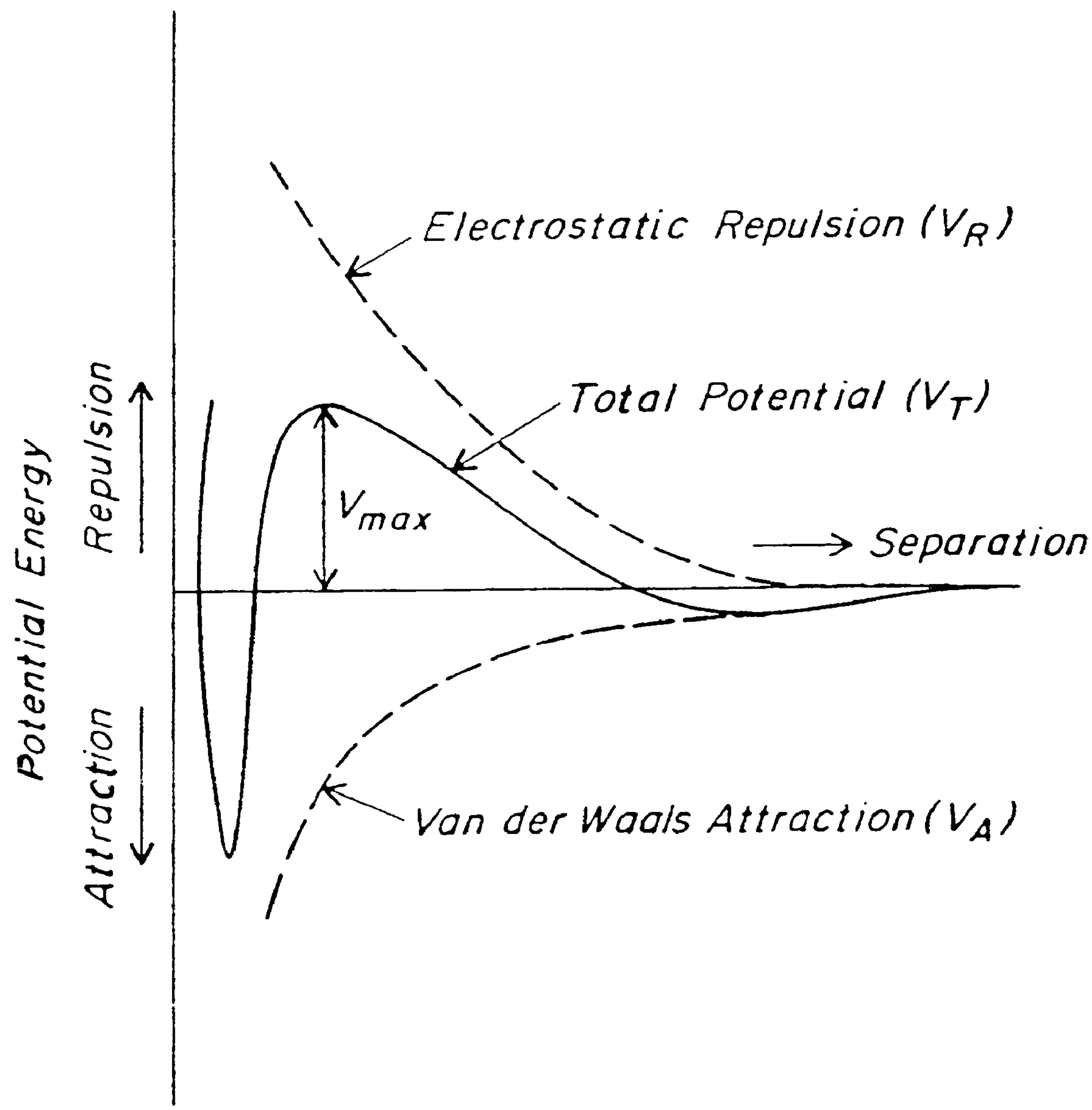
FIG. 1 is a representation of interparticle interaction energy as a function of the distance of separation between two particles.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Certain aluminum salts of low molecular weight fatty acids, for example aluminum triformate and aluminum triacetate, find applications in textile and leather processing, and paper manufacturing. U.S. Pat. Nos. 2,019,415, 5,468,892, 5,409,501 address various approaches for the manufacture of certain aluminum salts of these organic acids, i.e., aluminum triformate, yet aluminum triformate remains expensive and has limited commercial availability. In accordance with the present invention, there are described a novel group of compounds which are easily manufactured from readily available starting materials. Advantageously, the compounds of the present invention can be used as replacement(s) for the less readily available aluminum triformate in paper manufacturing and those applications previously listed. The present invention, therefore, describes processes for manufacturing these compounds and their use in the manufacture of a specialty grade of paper known as decor paper.

The present invention describes novel aluminum compounds with the following empirical formula:

$$AlX_{3-n}(Y)_n$$

wherein=0.01 to 2.99, preferably n=2 to 2.75. Each X, individually, can be an inorganic anion such as halides, alkoxides, hydroxide, nitrate, or perchlorate. In certain embodiments, X represents a combination of inorganic anions. The term "halide" includes iodide, bromide, fluoride, and preferably chloride. The term "alkoxide" is recognized by those skilled in the art and includes carbon alkyl chains of between 1 and 5 carbon atoms including, for example, methoxide, ethoxide, propoxide, iso-propoxide, butoxide, sec-butyloxide, tert-butoxide, and isomeric pentoxides.

Each Y, individually, can be an organic anion of an organic acid containing from one to six carbon atoms, including but not limited to, acetic acid, hydroxy-acetic acid, oxalic acid, succinic acid, citric acid, maleic acid, adipic acid, glutaric acid, and in particular formic acid. In certain embodiments, Y represents a combination of organic acid anions.

The invention further describes a simple and efficient process for the preparation of these products described above. The materials with such formulas are useful in decor paper manufacturing, as pigments, catalysts, size manufacturing, paper manufacturing, paint manufacturing, as well as, textile and leather processing.

Accordingly, the present invention describes improvements in the process for manufacturing decor paper. The properties required for high quality decor paper are include: High opacity—This feature is desired so that the surface beneath the decor paper does not contribute to the appearance of the decorative laminate; Good formation—This property insures sheet uniformity, as well as, a superior printing surface so that the finished surface of the decorative laminate has an attractive and unvarying appearance; Permanence of optical properties—This characteristic is desired so that the printed surface does not fade or yellow over time; Neutral sheet pH—This is the property which prevents resin systems from curing too quickly; and a Minimum basis weight—This feature is desired so that valuable raw materials are not wasted.

These properties are generally obtained by using a bleached chemical pulp with high loadings of a pigment, such as titanium dioxide as a secondary component. Decor papers contain titanium dioxide in the range from ten to forty-five percent, depending on the grade of paper. As discussed below titanium dioxide has been the pigment of choice for increasing the opacity of paper. However, the compounds disclosed herein improve the quality of the decor papers while optimizing opacity of the paper sheet and minimizing the basis weight and effect good paper formation while manufacturing a sheet at neutral sheet pH conditions.

Opacity is the property of a sheet that obstructs the passage of light and prevents observation of objects on the opposite side. Fine particle titanium dioxide is known to impart a high degree of opacity to paper and it is used as both a filler pigment and a coating pigment. Titanium dioxide is well suited for this purpose due to a number of unique physical properties. As noted by William Scott in, *Principles of Wet End Chemistry,* opacity is determined by light scattering and light reflectance. Four factors which play a key role optimizing opacity include: the greater the refractive index of a particle, the greater the light scattering potential; particles whose sizes are one half the wavelength of the incident light (i.e., a diameter of ca. 0.25 micron) scatter light the most extensively; the greater the number of optical interfaces available, the greater the potential for light scattering; the greater the difference in refractive index between the two materials forming a light scattering interface, the greater the light scattering at the interface.

Titanium dioxide has the highest refractive index of any commonly available material. At low loading levels, the increase in opacity is proportional to the amount of titanium dioxide added. However at higher loading levels, self-aggregation of titanium dioxide particles becomes a limiting factor. As mentioned above the difference in refractive indices at optical interfaces is an important factor in light scattering (i.e., materials with the same or similar refractive indices scatter little or no light). When pigment surfaces get closer than about 0.05 microns they come in "optical contact" and light scattering is no longer possible. Thus, uniform dispersion of titanium dioxide is important for the efficient development of opacity.

Self-aggregation or flocculation occurs when pigment particles agglomerate in a papermaking system. Aggregate titanium dioxide particles pack together closely and are especially prone to difficulties of this type. Thus, a primary objective in manufacturing decor papers is to maintain the furnish in an evenly dispersed state. This objective can be accomplished by controlling the electrical charges of the particles involved. The desired goal is to create a condition which maximizes pigment-fiber attraction, while minimizing pigment-pigment attraction. The compounds of the present invention help to minimize pigment-pigment attraction.

Although the current work is not bound by any theory of operation, several principles of wet end chemistry are relevant to manufacturing decor paper and to the present invention. As mentioned above the surfaces of the papermaking components have electrostatic charges. The surfaces of fibers used in papermaking have a negative electrostatic charge. The negative charges are present as a result of the carboxylic acid functions on the surface of the fiber. Consequently, the magnitude of these negative charges are pH dependent. At a pH of about 2.8 and lower the surface charge of fiber is close to zero. As the pH is increased, the surface charge becomes increasingly negative. The maximum negative charge on fiber surfaces is realized over the pH range of six to eight. Thus, the ideal operating conditions for obtaining a sheet with a neutral pH is an area where the fiber-fiber interaction is at its maximum repulsive force. By comparison, the surface charge of titanium dioxide is positive at low pH, but the charge decreases as the pH increases and at a pH of approximately six the surface charge becomes negative.

Ideally, decor papers should be manufactured at near neutral conditions so that the sheet has a neutral pH. Ideally, the fiber should have a surface charge at or near zero so that there is no fiber-fiber repulsion, and have a titanium dioxide surface charge that is positive so that the pigment particles repel one another. Under these conditions, the titanium dioxide would be uniformly dispersed through the sheet and "optical contact" would be minimized.

FIG. 1 represents the potential energy of fiber-fiber interactions as a function of distance. At or near neutral pH, the negative surface charges cause the fiber-fiber interaction to be repulsive as the fibers approach one another in the dewatering process.

This Coulombic repulsion stabilizes the furnish, making it difficult to remove the water from the dispersion. (The Coulombic force is represented by Line A. in FIG. 1.) At closer distances however, there is a second force known as Van der Waals Forces (i.e., hydrogen bonding) which cause an attractive fiber-fiber interaction. (The Van der Waals Forces are represented by the dashed line labeled Line B in FIG. 1.) The solid line in this figure represents the sum of the electrostatic repulsion (the negatively sloped dashed line) with the Van de Waals Attraction (positively sloped dashed line). The solid line indicates that as the fibers approach one another, the initial overall force is repulsive, but at closer distances the net force is attractive. FIG. 1 makes it apparent that if the surface charges are neutralized then the repulsive forces are reduced or eliminated, then the dewatering process in papermaking is facilitated. Thus, neutralizing the negative charges on the fiber leads to increased fiber-fiber attraction which in turn leads to improved formation.

The wet-end chemistry of the paper machine has a primary influence on the factors mentioned above. It is at this point in the papermaking process where a dilute aqueous dispersion of the papermaking components form into a sheet of paper. The process of neutralizing surface charges is called coagulation. Water soluble aluminum derived from alum is widely recognized as a highly effective coagulant. Water soluble aluminum is known to form highly charged polynuclear cationic species at pH greater than about 4.5. These species are thought to explain why the electrophoretic mobility of crystalline cellulose changes from negative to positive at a pH of about 5.8. For this reason alum is widely used in papermaking. However, alum is an acidic material and its use in manufacturing decor papers is limited because alum contributes to sheet acidity.

The methods of the present invention yield products which can be used as a substitute for aluminum triformate and/or aluminum tri-acetate. Accordingly the chemicals of the present invention are easily prepared from readily available raw materials. Moreover, compositions of the invention are more economical to produce than aluminum triformate and aluminum tri-acetate.

The invention provides methods for the preparation of compounds having the formula $AlX_{3-n}(Y)_n$ wherein each X, independently, can be a halide, an alkoxide, a hydroxide, a nitrate, a perchlorate or combinations thereof. Each Y, independently, can be ananion of an organic acid having one to six carbon atoms and the value of n is between about 0.01 and 2.99. The method includes combining between 4 moles and 5 moles of an organic acid having one to six carbon atoms acid with 1 mole of aluminum halohydrate. In preferred embodiments, the organic acid is formic acid or acetic acid and the aluminum halohydrate is aluminum chlorohydrate. Preferably, the method produces formic or acetic acid aluminum chlorides where n is between 2 and 2.75, preferably between 2.333 and 2.666. In a particularly preferred embodiment, the method produces an aluminum compound where X is a mixture of chloride and hydroxide and the organic acid is formic acid. Preferably the method produces formic acid aluminum compound/hydroxide/chloride mixtures where n is between 2 and, preferably between 2.333 and 2.666. The resulting product can be used in concentrated form or diluted to obtain a stable solution.

In another aspect, the present invention pertains to methods for preparing a compound having the formula $AlX_{3-n}(Y)_n$ wherein each X, independently, is a halide, an alkoxide, a hydroxide, a nitrate, a perchlorate or combinations thereof. Each Y, independently, is ananion of an organic acid having one to six carbon atoms and the value of n is between about 0.01 and 2.99. The methods include combining about 4 moles of an organic acid having one to six carbon atoms acid with 1 mole of polyaluminumhalide. In one embodiment, the organic acid is formic acid and wherein polyaluminum halide is polyaluminumchloride. In a preferred embodiment, the process produces an aluminum compound where X is chloride and Y is formate. The resulting product can be used in concentrated form or diluted to obtain a stable solution.

The present invention also pertains to decor paper which includes a wet strength resin, a pigment, a cellulosic material and an aluminum compound having the formula $AlX_{3-n}(Y)_n$ as described supra. Typical cellulosic materials include soft wood pulp (Kraft pulp, long fiber, pine) and/or eucalyptus pulp, known to those skilled in the art. Pigments include one of more of the pigments described above, including oxide yellow, oxide red, violet RL, and preferably titanium oxide. Wet strength resins are known to those skilled in the art and include Kymene and/or melanin resins.

The present invention further pertains to methods for preparing decor paper by combining a wet strength resin, a pigment, a cellulosic material and an aluminum compound having the formula $AlX_{3-n}(Y)_n$ as described supra and preparing a decor sheet from the decor sheet solution.

The following examples serve to further describe the invention. Analyses were performed by standard TAPPI methodology known to those of ordinary skill in the art.

EXAMPLE 1

Reaction of Aluminum Chlorohydrate with Five Moles of Formic Acid 59.3 grams of 90% formic acid (1.16 moles) were carefully added to a stirred solution of 100.7 grams of aluminum chlorohydrate solution (23.5% $Al_2O_3$, 0.2132 moles of aluminum chlorohydrate). The reaction was exothermic, the temperature of the solution increased from ambient to 140 degrees Fahrenheit. The theoretical yield was 72.95 grams of $Al_2Cl(O_2CH)_5$ (0.232 moles). The resulting solution was viscous at room temperature and had a specific gravity of 1.335 g/ml. The product was a stable solution for several days after which crystals began to form. Eight percent solutions of this composition were found to be stable for months at 40 degrees Fahrenheit. The product from this reaction is referred to as A5F in Example 5 below.

EXAMPLE 2

Reaction of Aluminum Chlorohydrate with Five Moles of Glacial Acetic Acid 69.60 grams of glacial acetic acid (1.16 moles) were carefully added to a stirred solution of 100.7 grams of aluminum chlorohydrate solution (23.5% $Al_2O_3$, 0.2132 moles of aluminum chlorohydrate). The reaction was only mildly exothermic, the temperature of the solution increased from ambient to 85 degrees Fahrenheit. The theoretical yield was 89.2 grams of $Al_2Cl(O_2CCH_3)_5$ (0.232 moles). The resulting solution was viscous at room temperature and had a specific gravity of 1.269 g/ml. Within hours the solution took on a cloudy appearance. Eight percent solutions of this composition were also cloudy.

EXAMPLE 3

Reaction of Aluminum Chlorohydrate with Four Moles of Formic Acid 47.4 grams of 90% formic acid (0.921 moles) were carefully added to a stirred solution of 100.7 grams of aluminum chlorohydrate solution (23.5% $Al_2O_3$, 0.2132 moles of aluminum chlorohydrate). The reaction was exothermic, the temperature of the solution increased from ambient to 132 degrees Fahrenheit. The theoretical yield was 66.46 grams of $Al_2OHCl(O_2CH)_4$ (0.232 moles). The resulting solution was viscous at room temperature and had a specific gravity of 1.353 g/ml. The product was a stable solution for several days after which crystals began to form. Eight percent solutions of this composition were found to be stable for months at 40 degrees Fahrenheit. The product from this reaction is referred to as A4FOH in Example 5 below.

EXAMPLE 4

Reaction of Polyaluminum Chloride (66% basic) with Four Moles of Formic Acid

66% basic polyaluminum chloride was prepared by adding 50.2 grams of aluminum chlorohydrate (23.5% $Al_2O_3$, 0.1156 moles) to a stirred solution 112.4 grams of 50% basic polyaluminum chloride (10.5% $Al_2O_3$, 0.1157 moles). The solution was allowed to equilibrate over a 30 minute period with stirring. Then, 47.3 grams of 90% formic acid (0.921 moles) were carefully added to this solution. The temperature increased to 108 degrees Fahrenheit. The theoretical yield was 70.52 grams of $Al_2Cl_2(O_2CH)_4$ (0.232 moles). The resulting solution was viscous at room temperature and had a specific gravity of 1.254 g/ml. The product was a stable solution for several days after which crystals began to form. Eight percent solutions of this composition were found to be stable for months at 40 degrees Fahrenheit. The product from this reaction is referred to as A4F in Example 5 below.

EXAMPLE 5

Samples from Examples 1, 3, & 4 (A5F, A4FOH and A4F) were compared to aluminum triformate for their efficacy in manufacturing decor paper. These tests were conducted using equimolar amounts of each of the materials evaluated. The evaluation in this example were performed under laboratory conditions. To insure that the evaluations gave representative results, six different grades of decor paper were included in the tests. The parameters evaluated in this example were zeta potential, furnish pH, sheet ash content, and sheet pH. The resulting decor papers were used to generate samples of decorative laminates. Visual inspection of the laminates were made to evaluate formation and optical properties.

Results

Table 1 shows the results for measurement of the zeta potential for each material in the six different grades of decor paper. These results demonstrate that both A5F and A4F have more positive zeta potentials than ATF. In the case of A4FOH, the zeta potentials were comparable to those of ATF or, in some cases more negative than ATF. From these tests it was concluded that A5F and A4F were better at controlling particle charges than ATF, while A4FOH was equivalent to or not as good as ATF.

TABLE I

| Zeta Potential Measurements (u/s/V/cm) | | | | |
|---|---|---|---|---|
| | ATF | A5F | A4F | A4FOH |
| Grade 1 | −8.1 | −7.1 | −4.6 | −9.2 |
| Grade 2 | −7.8 | −1.9 | −3.5 | −10.9 |
| Grade 3 | −12.0 | −7.1 | −7.2 | −11.6 |
| Grade 4 | 5.8 | 6.5 | 7.0 | 1.0 |
| Grade 5 | 11.3 | 11.2 | 9.3 | 5.3 |
| Grade 6 | 4.2 | 6.9 | 3.0 | 1.6 |

Table II demonstrates that the furnish pH for A5F and A4F is very similar to the furnish pH of ATF. A4FOH caused the furnish pH to be slightly higher than furnish pH when using ATF, but still well within acceptable limits.

TABLE II

| Furnish pH | | | | |
|---|---|---|---|---|
| | ATF | A5F | A4F | A4FOH |
| Grade 1 | 8.1 | 8.2 | 8.2 | 8.5 |
| Grade 2 | 7.4 | 7.3 | 7.3 | 8.0 |
| Grade 3 | 8.4 | 8.0 | 8.1 | 8.8 |
| Grade 4 | 8.0 | 7.9 | 7.8 | 8.5 |
| Grade 5 | 6.9 | 6.9 | 6.8 | 7.2 |
| Grade 6 | 6.9 | 6.8 | 6.7 | 7.1 |

Table III depicts the amount of ash in each of the sheets. The ash content indicates the amount of titanium dioxide present. This parameter is measure of filler retention. High ash content indicates improved retention and the likelihood of better runnability due to lower headbox ash content. The results in Table III indicate that all of the materials tested gave comparable results.

TABLE III

| Percent Sheet Ash | | | | |
|---|---|---|---|---|
| | ATF | A5F | A4F | A4FOH |
| Grade 1 | 26.4 | 26.0 | 25.7 | 25.4 |
| Grade 2 | 21.4 | 20.9 | 21.6 | 21.9 |
| Grade 3 | 28.9 | 29.1 | 28.9 | 29.7 |
| Grade 4 | 31.6 | 31.3 | 33.1 | 31.1 |
| Grade 5 | 33.5 | 33.5 | 33.5 | 33.2 |
| Grade 6 | 39.9 | 38.9 | 39.5 | 38.7 |

Table IV shows the measurement of the sheet pH. The results indicate that all four materials give acceptable performance.

TABLE IV

| Sheet pH | | | | |
|---|---|---|---|---|
| | ATF | A5F | A4F | A4FOH |
| Grade 1 | 8.0 | 7.4 | 7.5 | 7.5 |
| Grade 2 | 7.0 | 6.7 | 6.9 | 6.7 |
| Grade 3 | 6.8 | 6.5 | 6.7 | 7.0 |
| Grade 4 | 7.9 | 7.6 | 7.8 | 7.8 |
| Grade 5 | 6.4 | 6.6 | 6.3 | 6.5 |
| Grade 6 | 6.9 | 6.7 | 6.7 | 7.0 |

As mentioned above, the decor papers generated in these experiments were used to prepare samples of finished decorative laminate. These samples were inspected with a microscope to determine the extent of titanium dispersion in each of the laminates. The titanium dioxide in laminates made with A5F and A4F were found to be better dispersed than the titanium dioxide in laminates made with ATF and A4FOH. Improved pigment dispersion allows decor paper to be manufactured with lower titanium content without compromising the opacity. Thus, A5F and A4F offer the opportunity to realize additional cost savings by reducing pigment usage.

Comparison of Altriform (Aluminum Triformate) vs. A5F Lab Procedure

A. Preparation of slurry batches for hand sheets.

1. 250 ml of prepared pulp and $H_2O$ (with 2.5% fiber consistency) were placed in a bucket. The prepared pulp/$H_2O$ mix contains 20% soft wood pulp and 80% Eucalyptus. The water was at room temperature.
2. To determine the exact amount of pulp in the batch, the following procedure was utilized. Hand sheets were made in Frank Sheet Former Equipment Type 95854 with a backwater recycling system. 50 ml of pulp slurry were placed into a cup and about 350 ml of tap water were added. The pump was turned on, placing the operating switch into automatic position. The glass cylinder was closed and locked into position. The water discharge switch was placed into the freshwater position, with the drain valve on the holding tank in the open position. The volume probe was placed at the three (3) liter mark. The auto start button was activated and when freshwater reached the three (3) liter mark, the pulp slurry was added to the glass cylinder. After the water was drained and vacuum stopped, the glass cylinder was opened and a #1 pulp blotter was placed over the top side of sheet. The blotter was secured onto the sheet by rolling a felt-covered roller back and forth on the blotter two or three times. The screen unit was lifted off the stand and struck against the rubber mat to release the sheet from the screen. The sheet still attached to the #1 blotter was placed on a dryer unit. The #2 blotter was placed on the screen side of the sheet. A vacuum unit was started and lid closed, with a timer set for about 10 minutes. The dry sheets were weighed to determine gram weight and rounded to the second decimal point. This weight was multiplied by the total remaining amount of pulp slurry in the batch (5200). This value was divided by the 50 ml of content extracted to make the pulp sheet. The result was the amount of pulp in batch.
3. The following chemicals, $TiO_2$, color pigments, etc., were added to the bucket as follows. The percentages were based on 100% dry pulp in the batch, as calculated in step 2. The amount of each component in this example was based on the formula of grade 4.

Grade 4 with Altriform $H_2O$ pulp=1.31 gr.=50 ml, 5200 ml=136.24 gr. of pulp

Starting PH of pulp/$H_2O$ was about neutral 7.1. The components were added to the bucket in the following manner:

| | | | |
|---|---|---|---|
| Sodium Aluminate | 2.2407% | = 3.053 gr. | PH 10.8 |
| *$TiO_2$ I | 41.6296% | = 56.716 gr. | |
| *$TiO_2$ II | 16.5926% | = 22.606 gr. | |
| Oxide Yellow | .0267% | = .036 gr. | |
| Oxide Red | .0087% | = .012 gr | |
| Violet RL | .0013% | = .002 gr. | |

-continued

| | | | |
|---|---|---|---|
| **Altriform | .5926% | = .807 gr. | PH 9.2 |
| Kymene | 2.8733% | = 3.915 gr. | PH 9.0 |
| Altriform | .2447% | = 0.333 gr. | PH 8.2 |
| ***Kymene | 3.0365% | = 4.137gr. | PH 8.0 |

Grade 4 with A5F $H_2O$+pulp=1.30 gr.=50 ml, 5200=135.20 gr. of pulp

Starting PH of pulp/$H_2O$ was about neutral 7.1

| | | | |
|---|---|---|---|
| Sodium Aluminate | 2.2407% | = 3.029 gr. | PH 10.7 |
| *$TiO_2$ I | 41.6296% | = 56.283 gr. | |
| *$TiO_2$ II | 16.592% | = 22.433 gr. | |
| Oxide Yellow | .0267% | = .036 gr. | |
| Oxide Red | .0087% | = .012 gr. | |
| Violet RL | .0013% | = .002 gr. | |
| A5F (not diluted) | .5926% | = 1.296 gr. | PH 9.0 |
| Kymene | 2.8733% | = 3.885 gr. | PH 8.9 |
| A5F (not diluted) | .2447% | = .539 gr. | PH 7.9 |
| Kymene | 3.0365% | = 4.105 gr. | PH 7.9 |

*$TiO_2$ is specially designed for Decor paper application. $TiO_2$ I was Kameira, XR3 and $TiO_2$ II was DuPont, 974.
**For better solvency, Altriform was diluted in 40 ml of warm water with temperature of approximately 100° F. before adding to batch.
***Wet strength resin is based on cationic amine polymer - epichlorohydrin.

Mixing was performed while adding chemicals and pigments. Mixing was continued for 10 to 15 minutes after all ingredients were added. After this, mixing only occurred while drawing from the batch.

B. Procedure for building the hand sheets.

Two sheets 80 gr/$m^2$ were prepared by drawing off a desired amount of the mixture into two separate cups of equal volume. The first sheet was to create backwater for the second sheet. The second sheet was made with the backwater from the first sheet, with this sheet to be laminated.

1. The desired amount of mixture of equal volumes was placed into two separate cups. About 300 ml of cold tap water were added into each cup. The pump was turned on and the operating switch placed into the automatic position. The glass cylinder was closed and locked into position. The water discharge switch was placed into the fresh water position and the drain valve on holding tank was opened. The volume probe was placed at the three (3) liter mark, and the auto start button engaged. When freshwater reached the three (3) liter mark, the mixture of cup #1 was added to the glass cylinder, and the selector switch changed from the freshwater position to the backwater position and the drain valve on holding tank was closed. After water was drained and vacuum had stopped, the glass cylinder was opened, #1 pulp blotter was placed over top side of sheet, and the blotter was secured onto the sheet by a rolling felt-covered roller back and forth on blotter two or three times. The screen unit was lifted off of the stand and struck against the rubber mat to release the sheet from the screen. After the exhaust cycle has stopped, the glass cylinder was closed and secured. The volume probe was set at the six (6) liter mark and the process started. When the backwater reached the three (3) liter mark, the mixture from cup #2 was added to the glass cylinder; when the volume reached the six (6) liter mark, the selector switch was changed from the backwater to the freshwater position and the drain valve was opened on the holding tank. After water was drained and the vacuum was stopped, the glass cylinder was opened and #1 pulp blotter was placed over top of sheet. The blotter was secured onto the sheet by rolling a felt-covered roller back and forth on blotter two or three times. The screen unit was lifted off the stand and struck against the rubber mat to release the sheet form screen. The lid on the dryer unit was opened and sheet with #1 pulp blotter on was placed on the dryer unit with #2 pulp blotter placed on top of sheet. A vacuum was started and heat applied for about 10 minutes.

2. The sheet was weighed to obtain proper basis weight (gram weight is the best procedure to follow). Steps 1 and 2 were repeated until the correct basis weight was obtained. Volume was adjusted as required.

3. The sheet was marked with proper code and basis weight on screen side.

C. Laminating procedure.

1. Two matching basis weight hand sheets were selected for lamination. Each sample was identified with corresponding information relative to each batch, screen side up. Each sample was approximately 3" wide by 6" long.

2. High pressure resin mixture was prepared as follows:

a) 500 grams of 412 Cymel resin;

b) 500 mls of distilled $H_2O$;

c) water was brought to a boil, then both solutions were added to a high speed mixer/blender and mixed for 6 minutes;

d) The mixture was poured into a dipping tray (9"×12"×2") and allowed to cool to room temperature 70° F. (about 20 minutes);

e) 1 ml of muriate hardener was added and stirred until mixed thoroughly;

f) ½ ml. of Hypersol was added and stirred until mixed thoroughly;

g) The solution was allowed to stand for ten (10) minutes before use.

3. Saturating procedure.

a) Samples were attached to ball chips with screen side up;

b) Hand sheets were dipped into resin and held in resin for one (1) minute;

c) The hand sheets were removed from the resin and pulled through 0.8 mm wire wound rods at a moderate pace;

d) Samples were dried in an oven for approximately four (4) minutes at 120° F.

4. Lamination.

a) Samples were placed side-by-side with screen up on build-up as follows:
(6"×6" laminate)
Treated decor sheets
3" 40 lb. treater barrier
Three (3) treated Wilsonart core
(balance) 3" 40 lb. treated barrier
One (1) treated Wilsonart core
One (1) 6' 40 lb. treated barrier b) The build-up was placed between two (2) gloss plates;

c) A preheated press was used at 295° F. for final preparation. Samples were placed into press using 1100 psi pressure, with accruing time of ten (10) minutes and a cooling cycle time of five (5) minutes;

d) The laminates were removed when complete and the rough edges were trimmed with a cutter.

Those skilled in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A compound having the empirical formula $$AlX_{3-n}(Y)_n$$

wherein each X, independently, is a halide, an alkoxide, a hydroxide, a nitrate, a perchlorate or combinations thereof, and wherein at least a fraction of X is a halogen;

wherein each Y, independently, is a hydroxy acetic acid anion, an oxalic acid anion, a succinic acid anion, a citric acid anion, a maleic acid anion or a formic acid anion; and wherein the value of n is between about 0.01 and 2.99.

2. The compound of claim 1, wherein each halide, independently, is a chloride, a fluoride, a bromide, or an iodide.

3. The compound of claim 1, wherein each alkoxide, independently, is methoxide, ethoxide, isopropyloxide, propyloxide, butyloxide, sec-butyloxide, tert-butyloxide, or pentyloxide.

4. The compound of claim 1, wherein n is between about 2 and 2.75.

5. The compound of claim 1, wherein X is chloride and Y is formate.

6. The compound of claim 5, wherein n is between 2 and 2.75.

7. The compound of claim wherein n is between 2.333 and 2.666.

8. The compound of claim 1, wherein X is chloride and Y is acetate, and where n is between 1.2 and 2.75.

9. The compound of claim 8, wherein n is between 2 and 2.75.

10. The compound of claim 9, wherein n is between 2.333 and 2.666.

11. The compound of claim 1, wherein X is a mixture of chloride and hydroxide and Y is formate.

12. The compound of claim 11, wherein n is between 2 and 2.75.

13. The compound of claim 12, wherein n is between 2.333 and 2.666.

14. A method for preparing a compound having the empirical formula $$AlX_{3-n}(Y)_n$$

wherein each X, independently, is a halide, an alkoxide, a hydroxide, a nitrate, a perchlorate or combinations thereof, and wherein at least a fraction of X is a halogen;

wherein each Y, independently, is an anion of an organic acid having one to six carbon atoms;

wherein the value of n is between about 0.01 and 2.99, comprising the steps of combining between about 4 and 5 moles of an organic acid having one to six carbon atoms with 1 mole of aluminum halohydrate.

15. The method of claim 14, wherein said organic acid is formic acid or acetic acid and said aluminum halohydrate is aluminum chlorohydrate.

16. The method of claim 15, wherein n is between 2 and 2.75.

17. The method of claim 16, wherein n is between 2.333 and 2.666.

18. The method of claim 14, wherein X is a mixture of chloride and hydroxide and said organic acid is formic acid.

19. The method of claim 18, wherein n is between 2 and 2.75.

20. The method of claim 18, wherein n is between 2.333 and 2.666.

21. A method for preparing a compound having the empirical formula $$AlX_{3-n}(Y)_n$$

wherein each X, independently, is a halide, an alkoxide, a hydroxide, a nitrate, a perchlorate or combinations thereof;

wherein each Y, independently, is an anion of an organic acid having one to six carbon atoms;

wherein the value of n is between about 0.01 and 2.99, comprising the step of combining between about 4 and 5 moles of an organic acid having one to six carbon atoms with 1 mole of polyaluminumhalide.

22. The method of claim 21, wherein said organic acid is formic acid and wherein said polyaluminum halide is polyaluminumchloride.

23. The method of claim 22, wherein said X is chloride and Y is formate.

24. A compound having the empirical formula $$AlX_{3-n}(Y)_n$$

wherein X, independently, is a halide, an alkoxide, a hydroxide, a nitrate, a perchlorate or combinations thereof, and wherein at least a fraction of X is a halogen;

wherein each Y, independently, is an anion of an organic acid having three to six carbon atoms; and wherein the value of n is between about 0.01 and 2.99.

25. The compound of claim 24, wherein each halide, independently, is a chloride, a fluoride, a bromide, or an iodide.

26. The compound of claim 24, wherein each alkoxide, independently, is methoxide, ethoxide, isopropyloxide, propyloxide, butyloxide, sec-butyloxide, tert-butyloxide, or pentyloxide.

27. The compound of claim 24, wherein n is between about 2 and 2.75.

28. The compound of claim 24, wherein X is chloride.

29. The compound of claim 24, wherein n is between 2 and 2.75.

30. The compound of claim 29, wherein n is between 2.333 and 2.666.

31. The compound of claim 24, wherein X is a mixture of chloride and hydroxide.

32. The compound of claim 31, wherein n is between 2 and 2.75.

33. The compound of claim 32, wherein n is between 2.333 and 2.666.

* * * * *